US006485429B2

(12) United States Patent
Forstner (10) Patent No.: US 6,485,429 B2
(45) Date of Patent: *Nov. 26, 2002

(54) METHOD AND A DEVICE FOR NON-INVASIVE MEASUREMENT OF THE BLOOD PRESSURE AND FOR DETECTION OF ARRHYTHMIA

(75) Inventor: Klaus Forstner, Asperg/Wurttemberg (DE)

(73) Assignee: Microlife Intellectual Property GmbH, Berneck (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/317,122

(22) Filed: May 24, 1999

(65) Prior Publication Data

US 2001/0049476 A1 Dec. 6, 2001

Related U.S. Application Data

(60) Provisional application No. 60/087,077, filed on May 28, 1998.

(51) Int. Cl.[7] .................................................. A61B 5/00
(52) U.S. Cl. ........................ 600/494; 600/495; 600/500
(58) Field of Search ............................ 600/490, 492–6, 600/515, 518

(56) References Cited

U.S. PATENT DOCUMENTS

| | | | | |
|---|---|---|---|---|
| 4,261,370 A | * | 4/1981 | Van Nettlehorst | 600/515 |
| 4,262,674 A | * | 4/1981 | Uemura et al. | 600/493 |
| 4,356,827 A | | 11/1982 | Uemura et al. | |
| 4,531,527 A | * | 7/1985 | Reinhold, Jr. et al. | 600/515 |
| 4,566,463 A | * | 1/1986 | Taniguchi et al. | 600/494 |
| 5,056,527 A | | 10/1991 | Go et al. | |
| 5,253,648 A | * | 10/1993 | Walloch | 600/494 |
| 5,322,069 A | * | 6/1994 | Gallant et al. | 600/493 |
| 5,403,352 A | * | 4/1995 | Rossing | 607/4 |
| 5,680,867 A | | 10/1997 | Shimazu et al. | |
| 5,865,756 A | * | 2/1999 | Peel, III | 600/490 |
| 5,978,700 A | * | 11/1999 | Nigam | 600/515 |

FOREIGN PATENT DOCUMENTS

EP     0 841 034 A1    4/1997

OTHER PUBLICATIONS

Japanese Abstract, Section C. Sect. No. 1136, vol. 17, No. 65S, P. 117 (19931206).

* cited by examiner

Primary Examiner—Robert L. Nasser
(74) Attorney, Agent, or Firm—Shoemaker and Mattare (57) ABSTRACT

In a device or in a method for oscillometric measurement of the blood pressure, the pulse time differences are determined associated with the measurement of the blood pressure. Subsequent pulse time differences are stored in a storing unit (15). A distribution of pulse time differences is calculated in a calculating unit (16) and compared in a comparing unit (17) with predetermined reference values. If the distribution or the values of pulse time differences exceed a predetermined amount, an indication means (19) is activated which indicates existence of arrhythmic activities.

20 Claims, 7 Drawing Sheets

METHOD AND A DEVICE FOR NON-INVASIVE MEASUREMENT OF THE BLOOD PRESSURE AND FOR DETECTION OF ARRHYTHMIA

This application claims priorty from U.S. provisional patent application 60/087,077 filed May 28, 1998.

The invention relates to a method and a device for the non-invasive measurement of the blood pressure and for simultaneous detection of arrhythmia.

The clinical standard of measuring the arterial blood pressure is the auscultation of audible sounds during the release of an inflated cuff in the cubital region of the brachial artery. The method is called the Riva/Rocci method by analysis of the so-called Korotkoff pulse sounds. First, non-invasive blood pressure measuring devices automatically recorded the Korotkoff sounds by the integration of a microphone into the cuff design. Although these devices proved to be very accurate, the critical microphone positioning and the occurrence of artefact sounds limited the clinical use of this method. Detection of arrhythmia proves to be an important parameter for prevention of cardiac diseases. It is known in the art to determine arrhythmic activities by means of an electrocardiographic method. Since both arrhythmia and chronic hypertension is associated with a severe risk in establishing cardiovascular diseases such as arteriosclerosis and cerebral ischaemia, it is known to simultaneously measure the blood pressure of the patient and to detect arrhythmic activities by the use of an electrocardiogram.

From U.S. Pat. No. 4,262,674 it is known, to simultaneously measure the blood pressure based on Korotkoff sounds and to determine time differences between two consecutive pulses. The method according to this US patent is difficult to carry out because of the mentioned critical microphone positioning and the occurrence of artefact sounds. Further, the method according to the US patent is based on a strict consecutive treatment of measured pulses. The procedure does not analyse the total pulse pattern during the measuring time.

The oscillometric non invasive measurement of the arterial blood pressure has been clinically introduced at the beginning of the 1980s. The technology required a pneumatic pressure pulse detecting system and a microcomputer based signal analysis. Due to the fast technological progress on semiconductors, the devices were consequently equipped with smaller but more powerful microcomputers, programs and memories. In that way, the accuracy and stability of the non-invasive arterial blood pressure measurement was gradually improved.

The oscillometric method does not detect pulse sounds, but pressure changes within the cuff during the deflation process. The pressure pulses are generated by small amounts of streaming blood passing the vessels under the partially inflated cuff. Oscillometric devices avoid the use of a microphone and just require the application of a cuff at the patient's application site. For that reason, this technology was not only widely introduced clinically but was further integrated within a growing number of small blood pressure measuring devices, built for home use application.

Non-invasive oscillometric arterial blood pressure measuring units for home use were introduced widely towards the end of the 1980s. These devices measure and display three values: the arterial systolic pressure, the arterial diastolic pressure and finally the pulse frequency; all parameters are derived from the cuff application site.

The medical relevance of these devices is high. They are used in persons for whom regular measurements are recommended as a preventative measure, as well as in patients undergoing hypertensive or hypotensive blood pressure treatment. Since the age-dependent prevalence of hypertension is very high within the industrialised countries, regular blood pressure measurement serves as a crucial diagnosis measure to supplement the physician's diagnostic results.

As chronic hypertension is associated with a severe risk in establishing certain cardiovascular diseases, e.g. arteriosclerosis and cerebral ischaemia, a physiological adjustment of the arterial blood pressure—especially the diastolic arterial blood pressure—has been recognised as a highly efficient risk reduction of such disorders.

Further, a broad range of cardiac and extra-cardiac diseases are accompanied by rhythm disorders of the heart. This applies e.g. for diseases of the coronary arteries, diseases of the myocardial muscle, and disorders of the heart's excitation. In some cases, arrhythmia are significant early symptoms indicating the increased risk of developing certain severe heart malfunctions.

Some relevant arrhythmic heart activities are characterised by pathological variations of peripheral pressure pulse curves. So, pressure pulse curves may be used to identify certain arrhythmic events of the heart. Since pressure pulsations are monitored in the course of the oscillometric measurement, the analysis of the pulse pattern may be used to identify arrhythmic events. The analysis of the pulse rhythm is based on the analysis of pulse time difference, which is the time span between two correspondent pulse characteristics.

In case of a pathological rhythm status, pulse time differences may vary significantly in the course of the NIBP ("non-invasive blood pressure") measurement, or may be basically beyond physiological ranges. That means pulse time differences either change significantly or prove to be too high or too low. This is the basis of the detection of clinical relevant arrhythmia activities:

Supraventricular premature contractions: variation high due to pulse loss
Ventricular premature contractions: variation high due to pulse loss
Atrial fibrillation variation high due to absolute arrhythmia
Paroxysmal supraventricular tachycardia mean time difference low
Sinus-Tachycardia mean time difference low
Sinus-Bradycardia mean time difference high
Ventricular Bradycardia mean time difference high Some arrhythmic activities are unfortunately not noticed by patients, since the associated symptoms remain minimal. However, certain types indicate a severe forthcoming heart malfunction. For this reason, early diagnosis and therapy may diminish the risk of serious complications.

Arrhythmia are very common within the population of industrialised countries. For example about 0.5% of all adults, 3% of all people aged over 60, and 15% of all people over 70 suffer from atrial fibrillation.

It is an object of the present invention to overcome the drawbacks of the prior art, especially to provide a device and a method for simultaneously measuring blood pressure and detecting arrhythmic activities, which are both reliable and easy to apply, which are adapted for home use and which are easy to manufacture and carry out.

According to the present invention, these objects are solved with a method and a device according to the independent patent claims.

According to the invention, a pulse distribution is measured and is analysed by the device. The pulse distribution is investigated by using known medical criteria representing physiological or pathophysiological conditions, which are stored within the device. These criteria decide whether there is reason to diagnose an arrhythmic activity in the course of the NIBP measurement. Transformation, calculation and comparison can be effected analogically, digitally or by direct EDP comparison of curves. There can be signal storage and batchwise processing or on-line processing.

According to the method of the present invention, the blood pressure is preferably measured by measuring the pressure pulses of the blood in an artery by oscillometric measurement techniques. Measurement and analysis of the pressure pulses by oscillometric techniques allows the calculation of the blood pressure, especially the systolic and diastolic pressures. In order to indicate an arrhythmia, all values of the time difference between consecutive pulses are determined. The values of a plurality of consecutive pulse time differences are stored in a storing unit. The distribution of the pulse time differences is subsequently calculated in a calculating unit. In order to determine the existence of arrhythmic activities, the values and the distribution of the pulse time differences are compared with predetermined reference values and predetermined reference distributions of the pulse time differences in a comparing unit. In order to indicate the existence of arrhythmic activities, the comparing unit is caused to generate a signal if the values and/or distributions of the pulse time differences on the one hand and the predetermined arrhythmic specific values and distributions on the other hand are sufficiently close to each other. The signal can be optical, acoustic or any other kind of signal.

The method according to the invention is intended for a broad range of medical use. This includes the clinical application, the emergency based application, as well as home use. The indication of existence of arrhythmic activities tells the patient to consult a physician for a more detailed cardiac diagnosis.

The pressure pulse signals acquired by the oscillometric measurement are preferably amplified in a pulse pressure amplifier which generates an amplified signal. The amplified signal can subsequently be filtered and converted into a digital signal with an analogue/digital converter. Amplification and A/D conversion is known to those skilled in the art and is not the object of the present invention.

In a preferred embodiment, a pulse time difference histogram is generated in the calculating unit. Representation of the pulse time difference distribution in a histogram allows an especially reliable and precise detection of tie existence of arrhythmic activities.

The device according to the present invention substantially comprises a blood pressure monitor for indicating the blood pressure values and a cuff for the non-invasive oscillographic measurement of the blood pressure. The cuff is connected to the blood pressure monitor. A time difference measuring unit is used to determine the values of time pulse differences between two consecutive pulses. The device further comprises a storing unit for storing a plurality of consecutive time pulse differences which have been determined by the time difference measuring unit. The device is further provided with a calculating unit for calculating a statistic distribution of the time pulse differences and a comparing unit for comparing the values and the statistic distribution of the time pulse differences with predetermined reference values and reference distributions. The comparing unit is adapted to create a signal when the value and/or the distribution of the time pulse differences on the one hand and the predetermined value or reference distribution representing pathophysiological conditions on the other hand are sufficiently close to each other. It is also conceivable to create a signal if the difference between the measured parameters and criteria representing physiological values exceeds a certain amount.

The device comprises preferably a pulse pressure amplifier which creates an amplified pulse signal. The device further comprises a signal filter and optionally an A/D converter which filters and converts the amplified signal into a digital signal. The calculating unit is adapted to calculate a pulse time difference histogram. Such calculating units are known to those skilled in the art and are not the object of the present invention.

The device is preferably provided with indication means for indicating the existence of arrhythmia. Any kind of known indication means are possible—preferably, for instance, signal lamps, LEDs or an LCD display. It is also conceivable to provide acoustic indication means.

The apparatus detects arrhythmic activities during the non-invasive measurement of the arterial blood pressure. The apparatus uses a cuff which is wrapped around the patient's upper leg, lower leg, toe, upper arm, forearm or finger. After inflation of the cuff, the pressure is released gradually in order to measure arterial pulses by detecting pressure pulses. An inbuilt memory stores the pulse amplitudes of each pulse, the associated cuff pressure and the time differences between two consecutive pulses. While the first and second parameters are used to determine the systolic, mean and diastolic arterial blood pressure, the third parameter is applied in order to detect arrhythmic pulse activities of the patient. The detection includes premature ventricular and supraventricular contractions, absolute arrhythmia as well as tachycardia and bradycardia. The apparatus displays the result of the rhythmic analysis and indicates the user to take actions according to the result.

The analysis of the pulse time difference within a oscillometric measurement discloses the mean pulse time difference and the scattering of pulse time differences within one complete measurement cycle. Therefore the pulse time differences are investigated for every full measurement in order to detect possible arrhythmic activities.

The present invention analyses the pulse time difference signals derived from pulses within the pulse oscillogram. The analysis result is displayed beside the conventional values.

The invention will be more clearly understood with reference to the following figures, which show.

Figure 1:
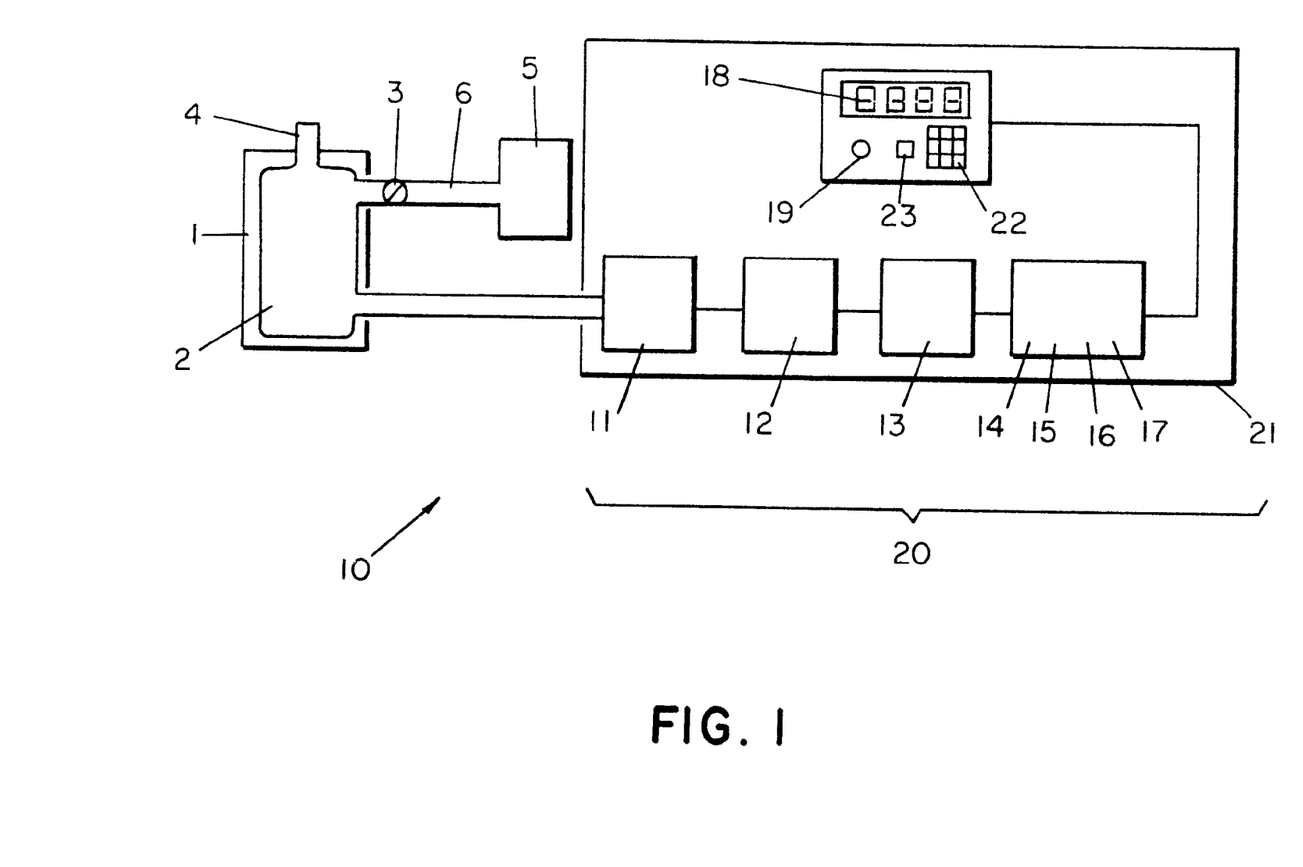
FIG. 1 a schematic view of a device according to the invention.

The oscillometric arterial pulse signals are derived from a non-invasive blood pressure measuring device 10, shown in FIG. 1.

In order to sufficiently amplify the measured pulse signals, the device 10 is equipped with a pulse pressure amplifier 11. In that way, the influence of various noise signals is reduced and weak pulse signals can be identified. Within this stage, signals which do not fulfil the criteria of a valid pulse are suppressed. For example, pulses which are too weak or which are increasing/decreasing too fast are suppressed as they are due to movement artefacts.

The low noise amplified signal is filtered in a signal filter 12 and consequently converted into a digital signal by means of an A/D converter 13.

The digital signal provided by the A/D converter 13 is subsequently used to determine the pulse time differences between two consecutive pulses in a time pulse difference measuring unit 14. The values of the time pulse differences are stored in a storing unit 15. A calculating unit 16 is provided for calculating a statistic distribution of the time pulse differences. This distribution and the value of the pulse time differences are subsequently analysed by using reference distribution and predetermined reference values within a comparing unit 17. If the measured distribution is close to a stored distribution representing a pathophysiological condition, an arrhythmia indicating signal will be generated. If the measured distribution is close to a stored physiological distribution, no signal will be generated.

The pulse amplifier 11, filter 12, A/D converter 13, time pulse difference measuring unit 14, storing unit 15, calculating unit 16 and comparing unit 17 together may form a signal processing unit 20. The components of the signal processing unit 20 are known to those skilled in the art and need not be explained in more detail.

The signal provided by the signal processing unit 20 is coupled to a blood pressure monitor 21. The blood pressure monitor 21 is provided with a first indication field 18 for indicating the blood pressure values, with a second indication field 23 concerning the pulse frequency display, and with a third indication field 19 for indicating existence of arrhythmic activities. The first indication field 18 consists of a LED or LCD display and the second indication field 19 consists of a signal lamp or signal LED which is activated if the comparing unit detects existence of arrhythmic activities.

Further the instrument is equipped with user keys 22, an optional electronically regulated pump 5 and a pneumatic system 6. The latter comprises a cuff 1 with a bladder 2, a possibly automatically controlled release valve 3 and a fast switching valve 4, which is actively used in order to instantly release the system pressure from cuff 1.

The pressure measurement, A/D conversion and the signal amplification may be performed by using several technology methods, e.g. pressure to frequency conversion, direct pressure to voltage conversion (Piezoelectric element) or any further known method.

The arrhythmia detection system may be implemented by using hardware and software system components. The arrhythmia detection is based on the analysis of pulse time differences. Pulse time difference are referred to as $T_p$. The reason for changes of pulse time differences are twofold:
1. Pulse time differences $T_p$ are constantly not in the physiological range.
2. The variation of pulse time differences $T_p$ is too high.

The judgement of the measurement's pulse time differences $T_p$ is performed by analyzing a pulse time difference histogram in the comparing unit 17, which is created during the measurement of the oscillometric pulses in the course of the non-invasive blood pressure measurement in the calculating unit 16.

Figure 2:
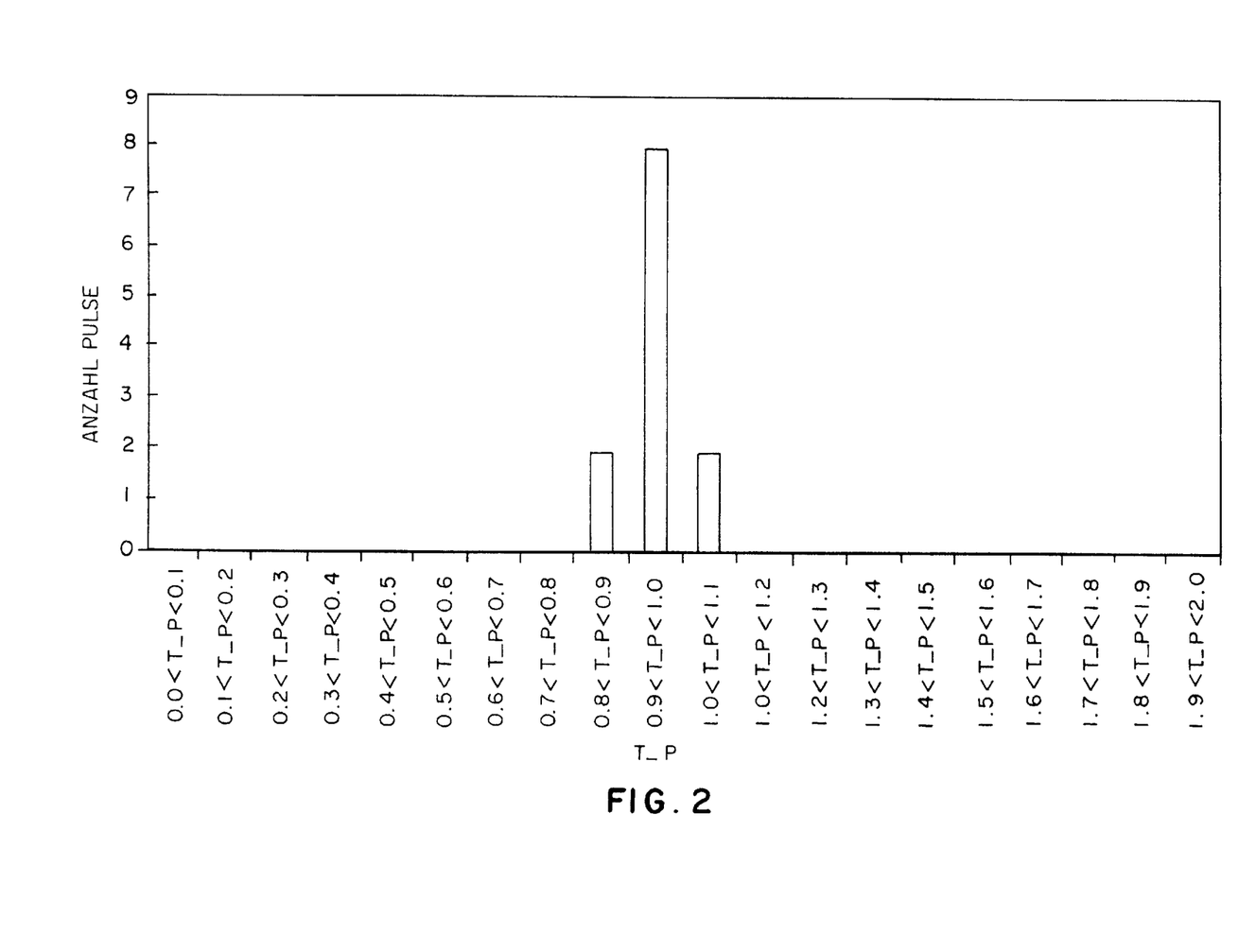
FIG. 2 a histogram of pulse time differences representing a standard physiological distribution.

An example of a physiological pulse oscillogram is shown in FIG. 2. The number of pulses is distributed around pulse time differences $T_p$ between 0.8 and 1.1 seconds. A maximum is to be found between 0.9 and 1.0 seconds. This physiological distribution represents the reference distribution around a reference value of about 0.9 to 1.0 seconds. Both the scale of the pulse time differences ad the number of pulses represent an example.

Figure 3:
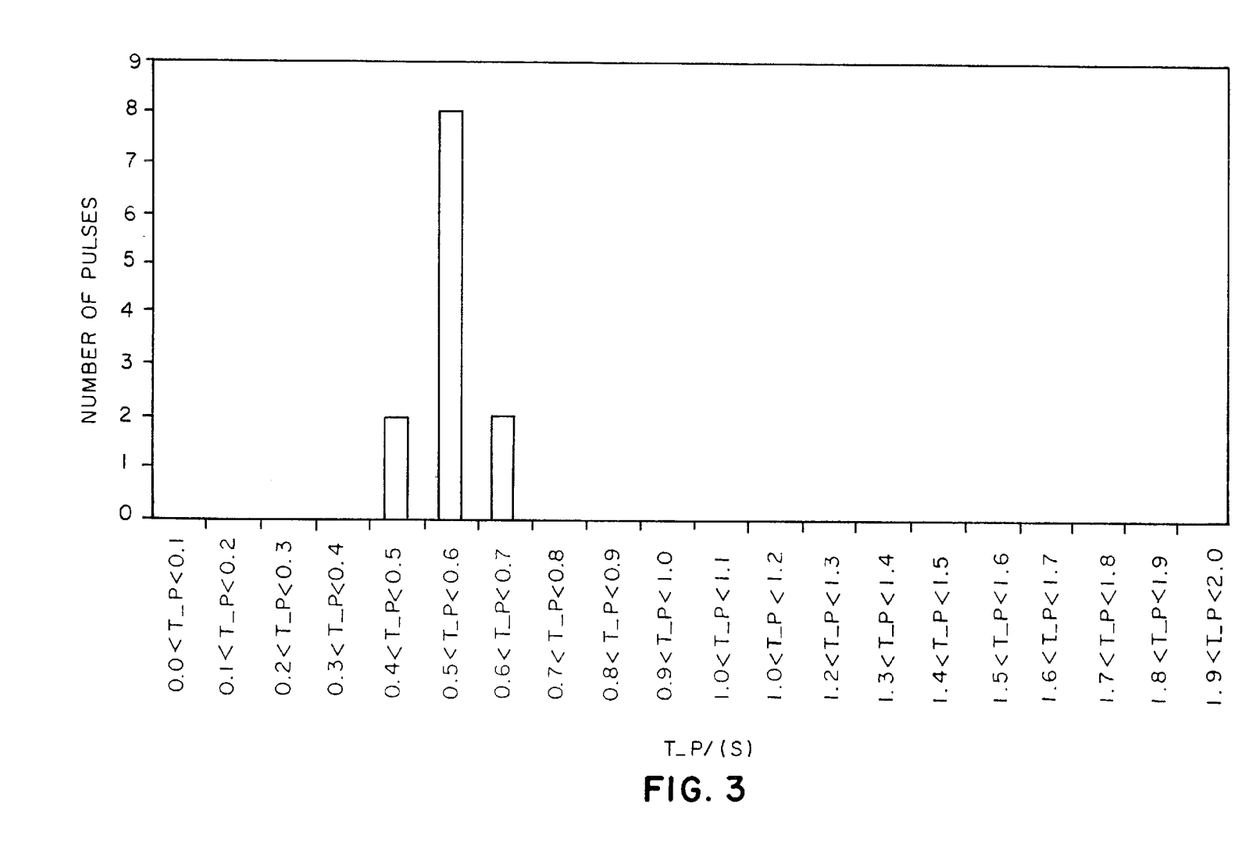
FIG. 3 a pulse time difference histogram representing tachycardia.
Figure 4:
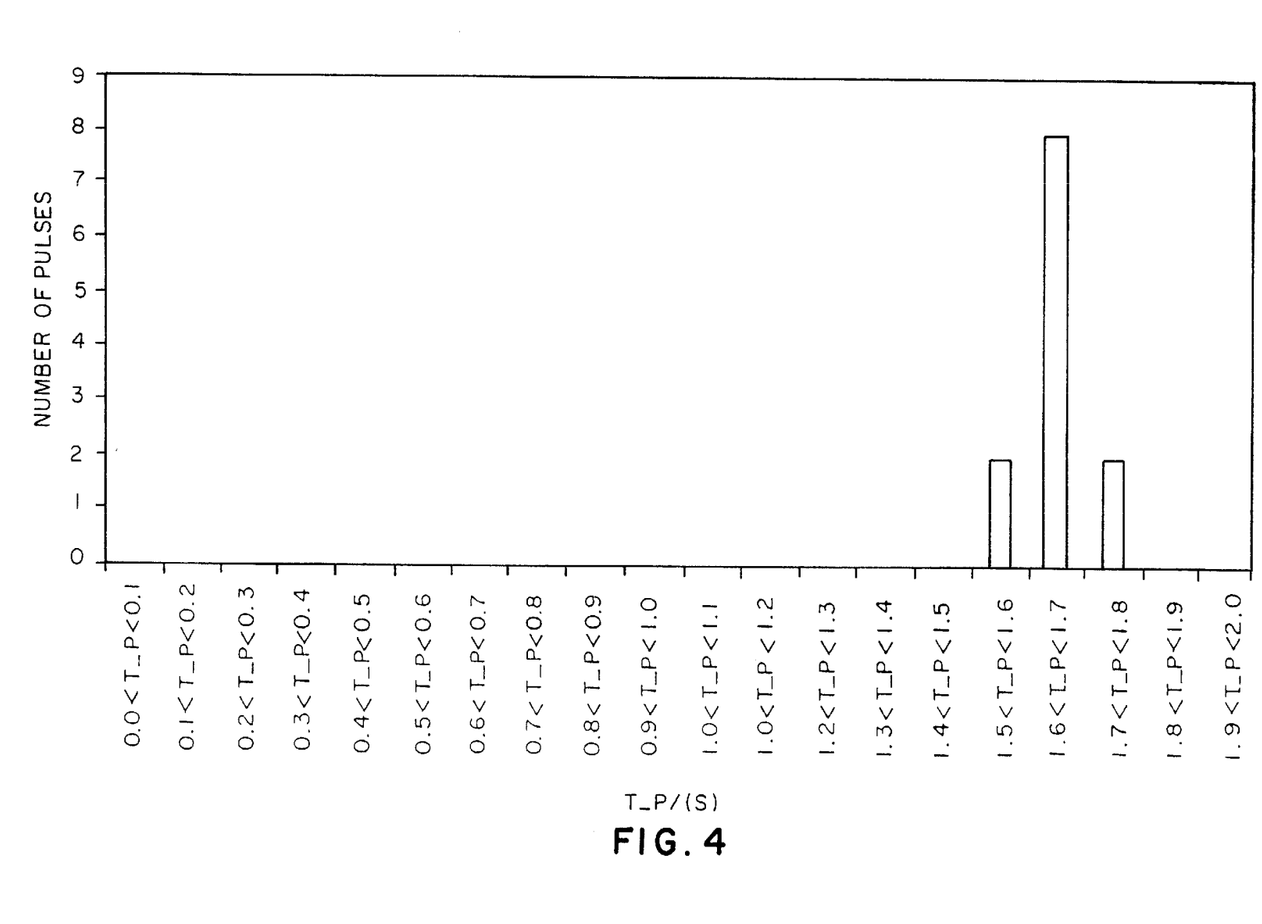
FIG. 4 a pulse time difference histogram representing bradycardia.

In FIGS. 3 and 4, pulse time differences are beyond the physiological limits. In FIG. 3 the centre pulse frequency exceeds 100 beats per minute (bpm), which clinically fulfils the criteria of tachycardia if the patient's frequency was investigated under rest conditions.

In FIG. 4, the pulse difference time histogram plots an example for a bradycardia. The centre frequency is smaller than 50 bpm.

Figure 5:
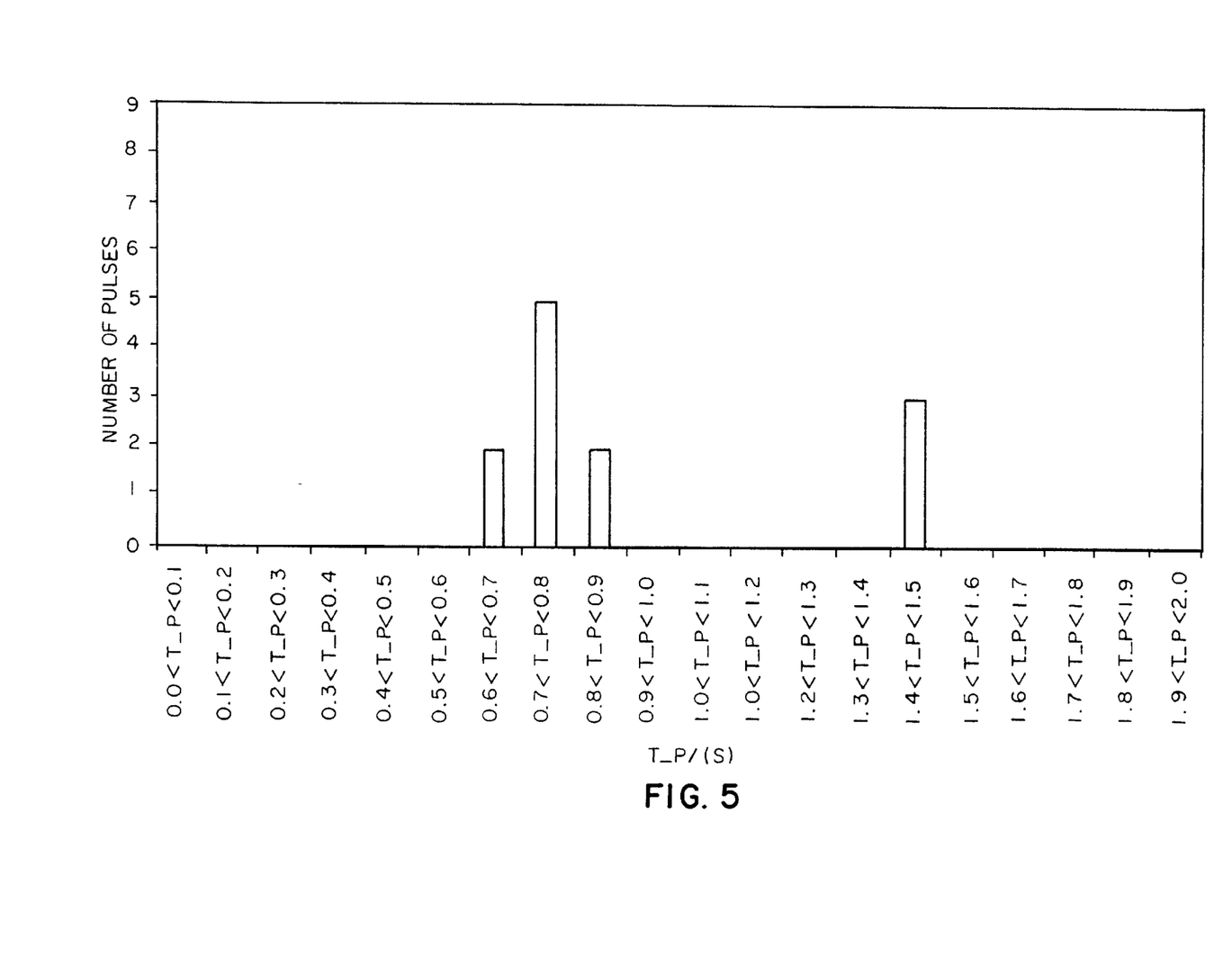
FIG. 5 a pulse time difference histogram representing missing pulses.

In FIG. 5 pulses are missing or cancelled by the filter criteria of the system (invalid pulse exclusion). This effect leads to the registration of doubled pulse time differences, which can be clearly seen from the pulse time difference registration. There are two peaks within the pulse time difference histogram. In the example given, there is a first histogram peak at time difference of about 0.75 seconds, which is equal to 80 bpm. Further, there is another peak at 1.5 seconds, which means about 40 bpm. This latter frequency is artificial and is a consequence of missing pulses. By detecting a second peak at the doubled value of the base pulse frequency, missing pulses can be identified, Missing pulses are clinically relevant as well as a frequent symptom. In particular, premature ventricular and supraventricular contractions are sources of missing pulses.

Figure 6:
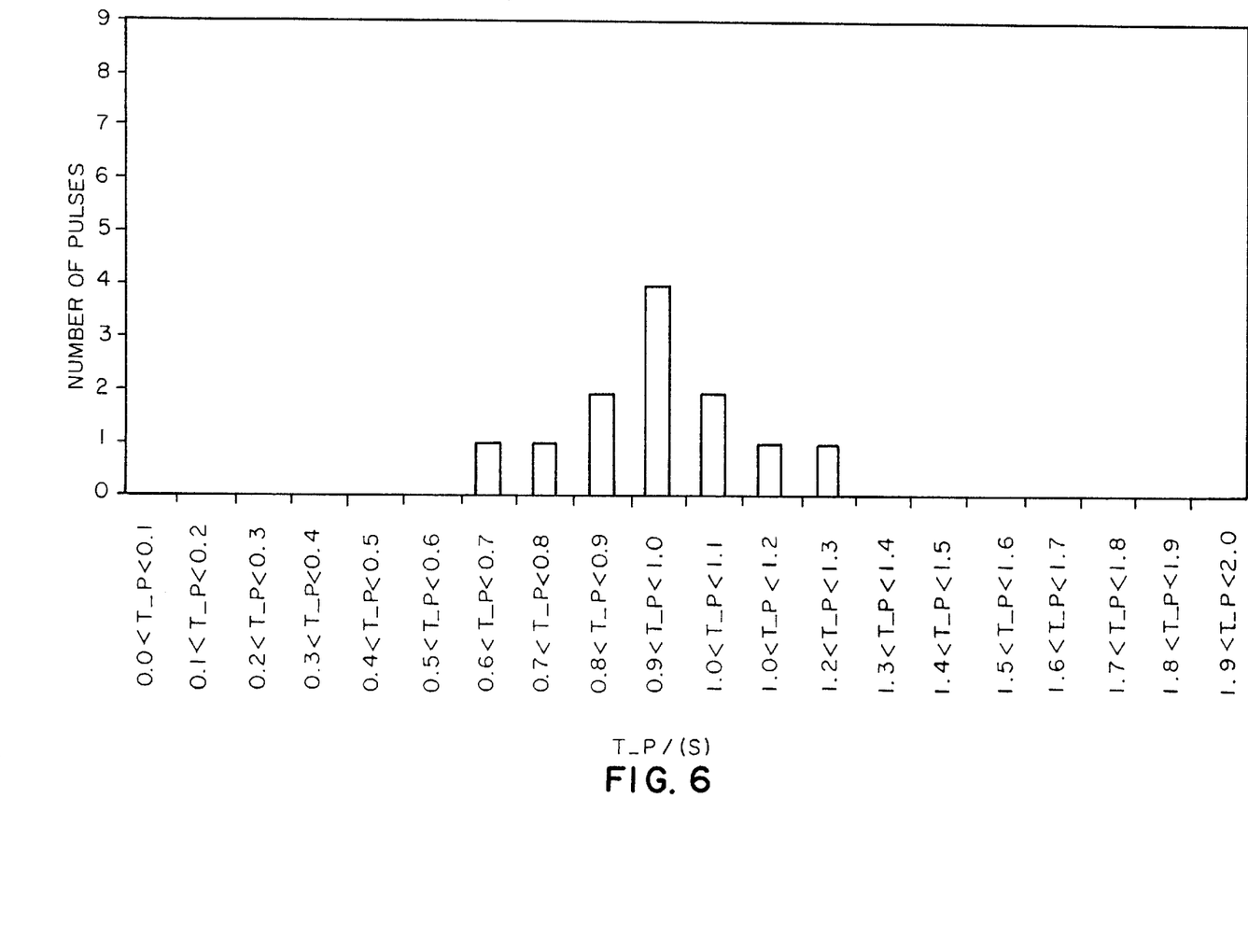
FIG. 6 a pulse time difference histogram representing absolute arrhythmia.

In FIG. 6 the pulse difference times vary widely. Within the example the pulse frequency changes continuously from 45 bpm to about 95 bpm. This high degree of variation is related to a so called absolute arrhythmia. This kind of an arrhythmia might be caused by atrial fibrillation. Atrial fibrillation is a frequent clinical symptom which has to be treated normally.

The pulse distribution within the pulse time difference histogram is applied in order to investigate arrhythmic actions within the pulse oscillogram.

The comparing unit 17 compares the distribution of the pulse time differences according to the example histograms of FIGS. 3 to 6 and the values of the pulse time differences with certain criteria which are related reference histograms. If a shift towards short pulse time differences (as in FIG. 3) is detected and the clinical criteria for tachycardia is fulfilled, the indication lamp 19 is activated and indicates existence of arrhythmic activities.

If the histogram is shifted towards high pulse differences as in FIG. 4 and the clinical criteria for bradycardia is fulfilled, the signal lamp 19 is also activated.

The signal lamp 19 is also activated if missing pulses as in FIG. 5 are detected or if the distribution is broadened due to an absolute arrhythmia as shown in FIG. 6. It is also conceivable to activate different signal lamps depending on the type of arrhythmia disclosed in one of the FIGS. 3 to 6. All these indications are derived according to known clinical criteria representing pathophysiological and/or physiological conditions, which are stored within the system.

Figure 7:
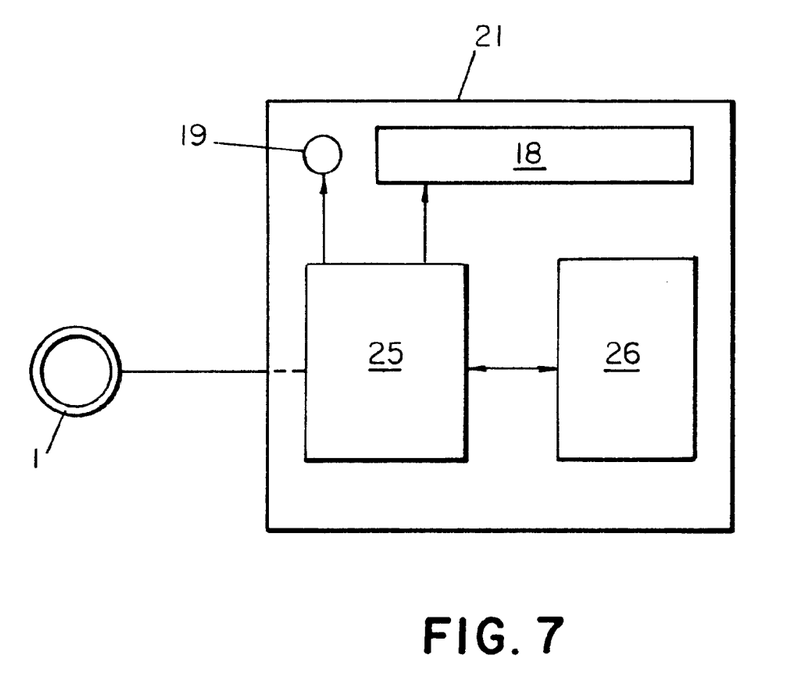
FIG. 7 shows the general principle of the invention

FIG. 7 discloses the general principle of the invention. Blood pressure pulses are oscillographically measured with a cuff 1, coupled into a CPU 25 and transformed into pulse signals. The pulse signals area treated in the CPU 25, temporarily stored in a memory 26 and compared with predetermined pulse signals.

The blood pressure and pulse frequency are displayed on a display 18 and a signal is activated if the difference between the measured pulse signal and predetermined pulse signals exceed a certain amount.

The system may further comprise a unit to determine the systolic and arterial blood pressure as well as the pulse frequency by analysing the pulse oscillogram. This unit also displays the measurement results and is controlled by the user.

What is claimed is:

1. A method for simultaneously measuring blood pressure and detecting pulse arrhythmia, said method comprising steps of
   detecting a plurality of consecutive blood pressure pulses in an artery with an oscillometric blood pressure monitor,
   measuring values of pulse time differences between said plurality of detected consecutive pulses,
   storing said values in a storage unit,
   calculating the distribution of said pulse time differences,
   comparing said distribution of the pulse time differences with a predetermined reference acceptable pulse time difference distribution, and
   generating a warning signal if the reference acceptable pulse time difference distribution differs substantially from the calculated distribution.

2. A method according to claim 1, comprising further steps of amplifying the pressure pulse signals in a pulse pressure amplifier, and excluding invalid pulses according to pulse acceptance criteria integrated in the pulse pressure amplifier.

3. A method according to claim 2, comprising further steps of filtering the amplified signal and converting it into a digital signal with an A/D converter.

4. A method according to claim 1, comprising a further step of generating a pulse time difference histogram in the calculating unit.

5. A device for simultaneously measuring blood pressure and detecting pulse arrhythmia, said device comprising
   a blood pressure monitor,
   a cuff connected to the blood pressure monitor,for non-invasively detecting blood pressure pulses,
   a time difference measuring unit for measuring values of time differences between successive pulses,
   a storage unit for storing a plurality of successive pulse time differences,
   a calculating unit for calculating a statistical distribution of said pulse time differences,
   a comparing unit for comparing said distribution of said pulse time differences with predetermined reference distribution, and
   means for generating a signal when said measured pulse time difference distribution differs substantially from said reference distribution.

6. A device according to claim 5, further comprising a pulse pressure amplifier.

7. A device according to claim 5, further comprising a signal filter and an A/D converter.

8. A device according to claims 5, wherein the calculating unit is adapted to calculate a pulse time difference histogram.

9. A device according to claims 5, further comprising means for indicating the existence of arrhythmia.

10. A device according to claim 9, wherein the indicating means includes at least one optical display.

11. A method for simultaneously measuring blood pressure and detecting pulse arrhythmia, said method comprising steps of
    detecting a pulrality of consecutive blood pressure pulses in an artery with an oscillometric blood pressure monitor
    measuring values of pulse time differences between said plurality of detected consecutive pulses,
    storing said values in a storage unit,
    calculating the distribution of said pulse time differences,
    comparing said distribution of the pulse time differences with a predetermined reference unacceptable pulse time difference distribution, and
    generating a warning signal if the reference unacceptable pulse time difference distribution does not differ substantially from the calculated distribution.

12. A method according to claim 11, comprising a further steps of amplifying the pressure pulse signals in a pulse pressure amplifier, and excluding invalid pulses according to pulse acceptance criteria integrated in the pulse pressure amplifier.

13. A method according to claim 12, comprising further steps of filtering the amplified signal and converting it into a digital signal with an A/D converter.

14. A method according to claim 11, comprising a further step of generating a pulse time difference histogram in the calculating unit.

15. A device for simultaneously measuring blood pressure and detecting pulse arrhythmia, said device comprising
    a blood pressure monitor,
    a cuff connected to the blood pressure monitor, for non-invasively detecting blood pressure pulses,
    a time difference measuring unit for measuring values of time differences between successive pulses,
    a storage unit for storing a plurality of successive pulse time differences,
    a calculating unit for calculating a statistical distribution of said pulse time differences,
    a comparing unit for comparing said distribution of said pulse time differences with a predetermined unacceptable reference distribution, and
    means for generating a signal when said meaasured pulse distribution does not differ substantially from said unacceptance reference dsitribution.

16. A device according to claim 15, further comprising a pulse pressure amplifier.

17. A device according to claim 15, further comprising a signal filter and A/D converter.

18. A device according to claim 15, wherein the calculating unit is adapted to calculate a pulse time difference histogram.

19. A device according to claim 15, further comprising means for indicating the existence of arrhythmia.

20. A device according to claim 19, wherein the indicating means includes at least one optical display.

* * * * *